United States Patent [19]

Guth et al.

[11] Patent Number: 4,511,513

[45] Date of Patent: Apr. 16, 1985

[54] DETERGENT COMPOUNDS AND COMPOSITIONS

[75] Inventors: Jacob J. Guth, Upper Black Eddy, Pa.; Robert J. Verdicchio, Succasunna, N.J.

[73] Assignee: Johnson & Johnson Baby Products Company, New Brunswick, N.J.

[21] Appl. No.: 375,073

[22] Filed: May 5, 1982

Related U.S. Application Data

[63] Continuation-in-part of Ser. No. 241,862, Mar. 9, 1981, abandoned.

[51] Int. Cl.[3] .................... C11D 1/52; C07C 103/54
[52] U.S. Cl. ................... 260/404.5; 252/117; 260/401; 260/403; 260/404; 560/251; 560/253; 562/564

[58] Field of Search .............. 260/404, 404.5, 401, 260/403, 404.5 PA, 404.5 Q; 252/117; 560/251, 253; 562/564

[56] References Cited

U.S. PATENT DOCUMENTS

| | | | |
|---|---|---|---|
| 2,781,376 | 2/1957 | Mannheimer | 260/404.5 R |
| 2,781,382 | 2/1957 | Mannheimer | 260/401 |
| 2,781,391 | 2/1957 | Mannheimer | 252/117 X |
| 2,970,160 | 1/1961 | Walker | 260/404.5 R |
| 3,070,600 | 12/1962 | Rudner | 252/117 |
| 3,198,822 | 8/1965 | Mannheimer | 260/401 X |
| 3,954,846 | 5/1976 | Grighard | 252/117 |
| 4,303,543 | 12/1981 | Mansy | 252/117 |

*Primary Examiner*—Thomas A. Waltz

[57] ABSTRACT

Novel amphoteric-fatty acid complexes are described as well as detergent compositions containing said complexes.

5 Claims, No Drawings

DETERGENT COMPOUNDS AND COMPOSITIONS

REFERENCE TO RELATED APPLICATION

This is a continuation-in-part of copending applications Ser. No. 241,862, filed Mar. 9, 1981 now abandoned.

BACKGROUND OF THE INVENTION

The present invention relates to amphoteric-fatty acid complexes. More specifically, the invention relates to amphoteric-fatty acid complexes which exhibit unexpected foam properties and low ocular irritancy. The invention further relates to detergent compositions containing the novel amphoteric-fatty acid complexes in combination with other surfactants and/or detergent components.

Nonirritating detergent compositions have been known in the art and have been in use for some time. U.S. Pat. Nos. 3,299,069 and 3,055,836 are merely two representative examples of such prior art nonirritating detergent compositions. Likewise, amphoteric compounds have been well known in the art and have been disclosed in use with various other detergent compounds. U.S. Pat. No. 2,528,380, discloses a ring structured amphoteric compound with a fatty acid attached to the ring nitrogen. None of the disclosures in the prior art disclose the amphoteric-fatty acid complexes of the present invention nor the advantages provided by same.

It is an object of the present invention to provide novel detergent compounds.

It is another object of the present invention to provide novel detergent compounds which exhibit good foam properties and low ocular irritancy.

It is a further object of the present invention to provide detergent compositions which exhibit good foam properties and low ocular irritancy.

These and other objects of the present invention will become apparent to one skilled in the art from the detailed description given hereinafter.

SUMMARY OF THE INVENTION

This invention encompasses non-zwitterionic, amphoteric-fatty acid complexes of the formula

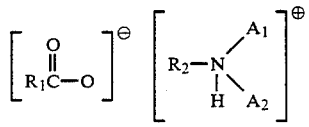

wherein $R_1$, $R_2$, $A_1$ and $A_2$ are as defined below.

DETAILED DESCRIPTION OF THE INVENTION

The present invention relates to novel non-zwitterionic, amphoteric-fatty acid complexes of the formula

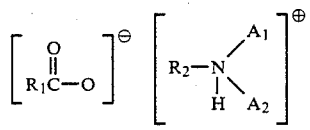

wherein $R_1$ is alkyl or substituted alkyl containing from about 5 to 17 carbon atoms and mixtures thereof;

$R_2$ is alkyl containing from about 6 to 18 carbon atoms and mixtures thereof or alkyl amido of the formula

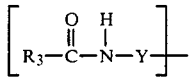

wherein $R_3$ is alkyl containing from about 5 to 17 carbon atoms, Z is H or lower alkyl containing from 1 to 4 carbon atoms; and Y is alkylene containing from 2 to 4 carbon atoms;

$A_1$ and $A_2$ are the same or different and at least one of $A_1$ and $A_2$ are selected from the group of anionic salt moieties consisting of the following:

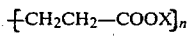

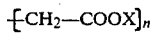

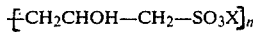

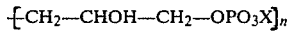

wherein X is a water-soluble cation such as $Na^+$, $K^+$, $Ca^{++}$, $Mg^{++}$ and the like and n is an integer of 1 or 2 with the proviso that if only one of $A_1$ and $A_2$ are selected from the anionic salt moieties above the other can be lower alkyl or lower hydroxyalkyl containing from 1 to 4 carbon atoms.

The non-zwitterionic, amphoteric compounds which are useful in the complexes of the present invention are of the formula:

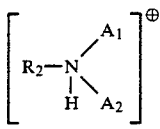

wherein $R_2$, $A_1$ and $A_2$ are as defined above.

These compounds can be prepared in accordance with the teachings of the art, see for example, U.S. Pat. No. 2,970,160, which is incorporated herein by reference.

The fatty acid compounds which are useful in the complexes of the present invention are of the formula:

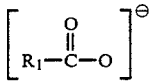

wherein $R_1$ is as defined above. These compounds are readily available commercially from numerous sources such as the fatty acids available from Emery Industries Inc., Cincinnati, Ohio, Procter & Gamble, Cincinnati, Ohio and various other commercial suppliers.

The amphoteric-fatty acid complexes of the present invention can be prepared by admixing a suitable non-zwitterionic amphoteric and a suitable fatty acid, utilizing heat, if necessary, to facilitate the blending and adding water, if needed. The ratio of fatty acid to amphoteric can be in the range of about 0.5:1 to 1.5:1, preferably about 1:1. The pH of the resulting complex should be within the range of 6.5–8.5, preferably within the range of 7.0–7.5, to minimize potential irritation problems.

Specific examples of the novel amphoteric-fatty acid complexes of the present invention include:

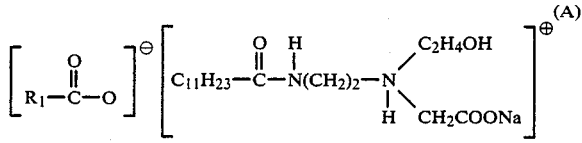

wherein $R_1$ is a mixture of alkyl chain lengths of from $C_5H_{11}$—$C_{17}H_{35}$.

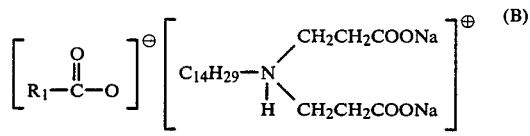

wherein $R_1$ is an 80%/20% mixture of tallow and coconut alkyl chain lengths.

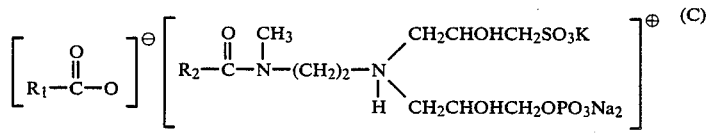

wherein $R_1$ is tallow alkyl chain lengths and $R_2$ is a $C_{11}H_{23}$—$C_{17}H_{35}$ mixture.

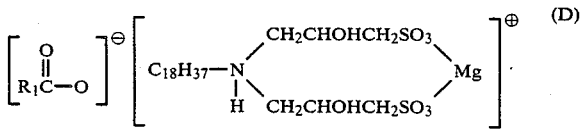

wherein $R_1$ is a 70%/30% mixture of lauric and myristic alkyl chain lengths.

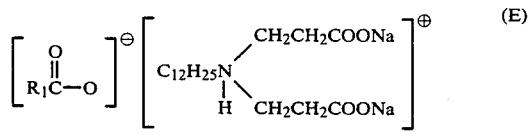

wherein $R_1$ is tallow alkyl chain lengths.

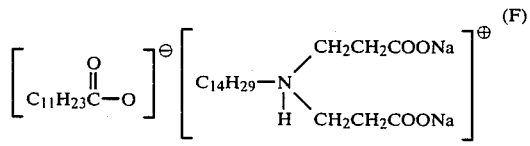

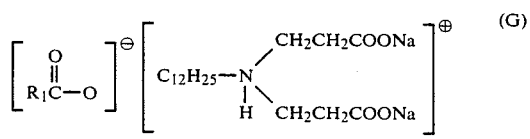

wherein $R_1$ is a mixture of alkyl chain lengths of from $C_5H_{11}$—$C_{17}H_{35}$.

The amphoteric-fatty acid complexes of the present invention exhibit excellent surfactant properties. In particular, these complexes exhibit good foam properties and low ocular irritancy. The good foam properties are unexpected because fatty acids do not normally exhibit such properties at pH values below 9. It has further been found within the pH range of 7.0–7.2 that the amphoteric-fatty acids complexes exhibit unexpected foam synergism.

These complexes can be utilized in detergent compositions either alone or in combination with other surfactants in a range of from about 1.0 to 50.0% by weight of the total compositions.

The amphoteric surfactants which may be used in conjunction with the fatty acid amphoteric complexes of the present invention include betaines, sultaines, phosphobetaines, phosphitaines, n-alkylamino propionates, n-alkylimino dipropionates and imidazolines. The betaine and sultaine surfactants useful in this invention are described in U.S. Pat. No. 3,950,417 issued Apr. 13, 1976, which is incorporated herein by reference. The phosphobetaines and phosphitaines useful in this invention are described in U.S. Pat. No. 4,215,064 and 4,261,911, both of which are incorporated herein by reference. The n-alkylamino propionates and n-alkylimino dipropionates are sold under the tradename Deriphats by General Mills. The imidazolines which are useful in the compositions of this invention are described in U.S. Pat. No. 2,970,160, which is incorporated herein by reference.

The preferred betaine amphoteric surfactants include the alkylbetaines such as cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl)carboxymethylbetaine, oleyldimethyl-gamma-carboxypropylbetaine, lauryl-bis-(2-hydroxypropyl)-carboxyethylbetaine, and the like; the sultaines such as cocodimethylpropylsultaine, stearyldimethylpropylsultaine, lauryl-bis-(2-hydroxyethyl)propylsultaine and the like; and the amidosultaines such as cocoamidodimethylpropylsultaine, stearylamidodimethylpropylsultaine, laurylamido-bis-(2-hydroxyethyl)propylsultaine, and the like.

The preferred phosphobetaines include lauric-myristicamido-3-hydroxypropylphosphobetaine, cocamidodisodium-3-hydroxypropylphosphobetaine, lauric-myristicamidodisodium-3-hydroxypropylphosphobetaine, lauric-myristicamidoglyceryl-phosphobetaine, lauric-myristicamidocarboxydisodium-3-hydroxypropylphosphobetaine, and the like. The preferred phosphitaines include cocoamidopropylmonosodiumphosphitaine, lauric-myristicamidopropylmonosodiumphosphitaine and the like.

The preferred n-alkylamino propionates and n-alkylimino dipropionates include those having the following structures:

and

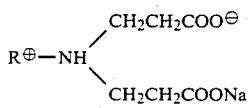

wherein R is alkyl of from about 8 to 22 carbon atoms and mixtures thereof.

The amphoteric detergents may be present in an amount from about 2 to 10% by weight of the total composition.

It is envisioned that any anionic surfactant may be used in the compositions of the invention such as, for example, an alkyl sulfate of the formula $R-CH_2-OSO_3X$, an alkylether sulfate of the formula $R(OCH_2CH_2)_p-OSO_3X$, an alkylmonoglyceryl ether sulfonate of the formula

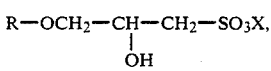

an alkylmonoglyceride sulfate of the formula

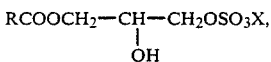

an alkylmonoglyceride sulfonate of the formula

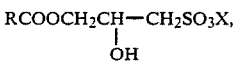

an alkyl sulfonate of the formula

and an alkylaryl sulfonate of the formula

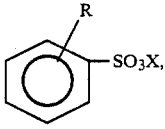

wherein R is alkyl having from 7 to 18 carbon atoms; X is selected from the group consisting of alkali metal ions, alkaline earth metal ions, ammonium ions, and ammonium ions substituted with from 1 to 3 lower alkyls and p is an integer from 1 to 6.

It has also been found that when anionic surfactants containing at least one carboxylic acid moiety are utilized the specific amphoteric-fatty acid complexes of the present invention in a ratio of from 1:4 to 4:1 there results a synergistic mixture with respect to foam height and quality.

The specific anionic surfactants contain at least one carboxylic acid moiety and are selected from the group consisting of sulfosuccinates, alkyl carboxylates, α-sulfo fatty acid and ester carboxylates, alkyl succinates, acyl sarcosinates and fatty acid protein condensates. All of these compounds are well known in the art and can be prepared according to well-recognized processes.

The sulfosuccinates are of the general formula

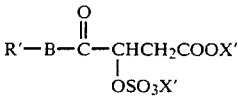

and can be prepared by reacting maleic acid with a suitable fatty alcohol followed by the addition of NaHSO₃ to the double bond.

The α-sulfo fatty acid and ester carboxylates are of the following general formuli respectively

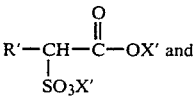

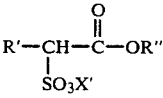

and can be prepared by sulfonation of the suitable fatty acids and esters.

The alkyl carboxylates are of the following general formula $$R'-O[(CH_2)_2O]_q-CH_2COOX'$$

and these compounds can be prepared by the Williamson ether synthesis which involves reacting an alkoxide with sodium chloroacetate.

The alkyl succinates are of the general formula

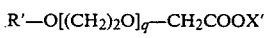

and are the reaction product of a suitable fatty alcohol with succinic acid or succinic anhydride.

The acyl sarcosinates are of the general formula

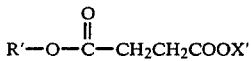

and are the reaction product of a suitable fatty acid with a lower substituted amine such as glycine or N-methyl glycine.

The fatty acid protein condensates are of the general formula

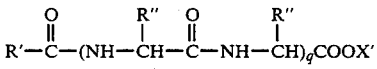

and are the reaction products of a suitable fatty acid with an amino hydrolysate.

In the above specific anionic surfactants, R' is alkyl containing from about 8 to 18 carbon atoms; R" is lower alkyl of from about 1 to 5 carbon atoms; B is O, N or $O-(CH_2-CH_2O)_m$ wherein m is an integer of from 1 to 5; X' is H+ or a water soluble cation such as Na+, K+, Ca++, Mg++ and the like; q is an integer of from 1 to 100; and Z is H or lower alkyl containing from 1 to 4 carbon atoms.

Specific examples of suitable anionic surfactants include:

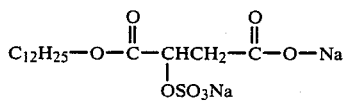 (AA)

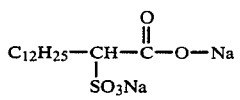 (BB)

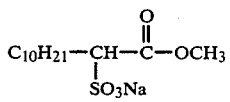 (CC)

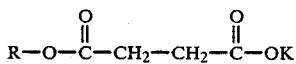 (DD)

wherein R is 50/50 mixture of $C_{12}H_{25}$—$C_{14}H_{29}$

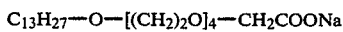 (EE)

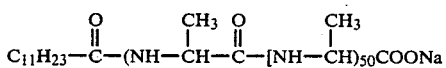 (FF)

The anionic detergent may be present in an amount of from about 2 to 50% by weight of the total composition.

Nonionic detergents which are useful include the alkylene oxide ethers of phenols, fatty alcohols, and alkyl mercaptans; the alkylene oxide esters of fatty acid amides; the condensation products of ethylene oxide with partial fatty acid esters, and mixtures thereof. The polyoxyalkylene chain in such agents may contain from 5 to 100 alkylene oxide units in which each alkylene unit has from 2 to 3 carbon atoms.

The nonionic surfactant may be present in an amount of from about 1 to 30% by weight of the total composition.

Cationic surfactants suitable in these compositions include mono- and bis-quaternary ammonium halides, such as stearyldimethylbenzylammonium chloride, cetyltrimethylammonium chloride, N,N-dioctadecyl-N,N,N',N'-tetramethyl-1,5-(3-oxapentylene)diammonium bromide; tertiary amine salts such as cocoamidopropyldimethylamine hydrochloride stearylamidopropyldimethylamine citrate; cationic polymers such as hydroxyethyl cellulose reacted with epichlorohydrin and then quaternized with trimethylamine (Polymers of this type are sold by Union Carbide under the tradename Polymer JR) and specific triesters of phosphoric acid. The specific triesters of phosphoric acid are described in copending patent application Ser. No. 59,838 filed July 23, 1979, now abandoned, which is incorporated herein by reference. The cationic surfactants should be present in an amount of from about 0.5 to 3.0% by weight of the total composition.

The total amount of the active surfactant ingredients in the present invention should not be greater than about 50% by weight of the total composition in order to avoid ocular irritation problems, preferably from about 5 to 20% by weight of the total composition with the proviso that the total amount of anionic surfactant and amphoteric surfactant should not exceed 20% by weight of the total composition. In addition, other ingredients conventionally added to surfactant compositions for personal use, such as dyes, preservatives, perfumes, thickeners, opacifiers, conditioners, emollients, buffering agents, and the like, may be added in minor amounts. Ingredients such as dyes, preservatives and perfumes together usually constitute less than 2% by weight of the total composition and thickeners may be added to the composition in an amount of from about 1 to about 3% by weight of the total composition.

The detergent compositions of the present invention should have a pH in the range of about 6.5 to 8.5, preferably from about 7.0-7.5 and most preferred from about 7.0-7.2.

Liquid detergent compositions utilizing the complexes of the present invention can be prepared by admixing the amphoteric-fatty acid complex with the other surfactant(s) at room temperature or slightly elevated temperatures (about 50° C.) and then sufficient deionized water is added to bring the composition to about three quarters of its intended weight. Other ingredients such as various detergency adjuncts, fillers, carriers, perfumes, preservatives, gelling agents and the like are added as required followed by the balance of the water. The pH is then adjusted to within the desired range by the addition of strong acid, e.g., HCl, or strong base NaOH, as needed.

Detergent bar compositions utilizing the complexes of the present invention can be prepared by admixing the amphoteric-fatty acid complex with the other surfactant(s) in a steam jacketed rotary mixer at temperatures within the range of 60°-80° C. Fillers, whitening agents and processing oils can be added, as needed, to the hot slurry. After adequate mixing to assure homogeneity and moisture balance the product is chill rolled or drum dried into flakes. Dyes and fragrances are added to the flakes in a standard amalgamator together with additional water to provide proper bar formation. After adequate mixing the flakes are milled and plodded into logs which are then cut into blanks prior to stamping into bar form.

The detergent compositions of the present invention can be tested for ocular irritation by the following modified Draize Test (J. H. Draize et al., Toilet Goods Assn. No. 17 May 1952, No. 1, Proc. Sci. Sect.).

An 0.1 ml. sample of a neutral composition under test is dropped into one eye of an albino rabbit, the other eye serving as a control. Six rabbits are employed for each composition. Observations are made after 1, 24, 48, 72 and 96 hours and 7 days after initial instillation; second and third instillations are made after the 24 and 48 hour readings. Results may vary from substantially no change or only a slight irritation in the appearance of the rabbit's eye after 7 days to severe irritation and/or complete corneal opacity. Ocular lesions are scored for the cornea, iris and conjunctiva with a higher number indicating greater ocular irritation and the scores are added to give a total numerical value for each reading for six rabbits and averaged. The averaged score is an indication of the irritation potential of the composition under test. Based on the averaged score, descriptive irritation evaluation may be given, e.g., none, slight, moderate, severe, as the case may be.

Detergent compositions of the invention provide high foam volume and moreover outstanding foam stability as measured by an adaption of the well-known Ross-Miles foam test principle "Oil and Soap" 18.9–102 (1941):

Lanolin, anhydrous, cosmetic grade is mixed with dioxane (technical grade) in the proportion of 2.5 grams lanolin and 100 grams of dioxane. The lanolin is first mixed with 25 cc. of dioxane. This mixture is heated over a steam bath to 45° C. in order to dissolve the lanolin in the dioxane. The remainder of the dioxane is then added and mixed. This lanolin dioxane solution, which is stored in an amber bottle, should be prepared fresh on the day that the tests are run.

The composition to be tested is diluted by adding 376 cc. of distilled water to 4 grams of the composition, and then by adding 20 cc. of the lanolin-dioxane solution described above while mixing. Heat is produced when the lanolin-dioxane solution is added to the solution of the composition in water and care must be taken in adjusting the temperature of this solution to 24°-25° C. Both of these intermediate solutions should therefore be adjusted to 23° C. before mixing. The cooling of the lanolin-dioxane solution should be gradual in order to avoid precipitation of the lanolin. This will produce a final solution with a temperature of 24°-25° C.

The final solution of the composition to be tested, water, dioxane and lanolin described above, is then run in a modified Ross-Miles foam column in the usual way. All tests are conducted in duplicate, and the average of the two results is taken. Foam stability is determined by measuring the decay in foam height after two minutes, expressed as a percentage of the original height.

Specific embodiments of the present invention are illustrated by the following representative examples. It will be understood, however, that the invention is not confined to the specific limitations set forth in the individual examples, but rather to the scope of the appended claims.

EXAMPLE I 320.2 grams (0.19 g. moles) of a 24% active solution of an amphoteric of the formula

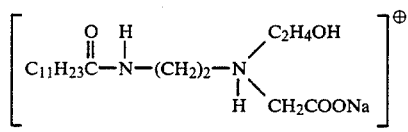

are mixed with 47 grams (0.24 g. moles) of premelted coconut fatty acids of the following chain length percentage distribution: $C_6$—0.3, $C_8$—7.3, $C_{10}$—6.5, $C_{12}$—50.7, $C_{14}$—18.9, $C_{16}$—8.6, $C_{18}$—7.7.

The resulting product is an opaque, viscous slurry containing 34% solids with a pH of 7.1 and is an amphoteric-fatty acid complex of the structure shown as compound A in the specification. The complex foams copiously in both soft and hard water and is a slight ocular irritant.

EXAMPLE II

The slurry obtained in Example I is freeze-dried by known procedures to yield about 95% solids. The solids are ground to a slightly tacky powder which can be utilized to form a bar soap and is a slight to moderate ocular irritant.

EXAMPLE III

Following the procedures of Example I, the amphoteric of Example I is mixed with stripped hydrogenated coconut fatty acids of the following chain length percentage distribution: $C_8$—1, $C_{10}$—1, $C_{12}$—56, $C_{13}$—24 $C_{16}$—12.5 and $C_{18}$—5; to form the desired amphoteric-fatty acid complex shown as compound A in the specification. The resultant dried powder is found to be a slight ocular irritant.

EXAMPLE IV

Following the procedures of Example I, 227 grams (0.15 g. moles) of a 22% active solution of tetradecyliminodicarboxylate are dissolved in 450 grams of deionized water at a temperature of about 50°-60° C. 30 grams (0.15 g. moles) of the coconut fatty acid of Example I are added to form the resulting amphoteric-fatty acid complex which is a moderate irritant and is of the following structure:

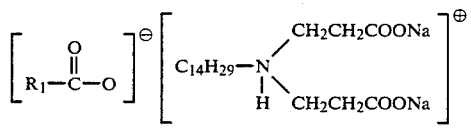

wherein $R_1$ is a mixture of alkyl chain lengths of from $C_5H_{11}$—$C_{17}H_{35}$.

EXAMPLE V 300 grams (0.07 g. moles) of an 11.1% active solution of an amphoteric of the formula

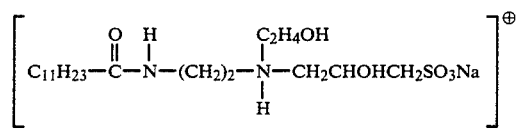

are mixed with 14.1 grams (0.07 g. moles) of premelted coconut fatty acids having the alkyl chain length distribution set forth in Example I. The resulting product is a hazy solution containing 15% solids, having a pH of 7.3 and is an amphoteric-fatty acid complex of the formula:

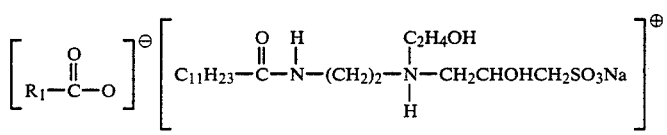

EXAMPLE VI 360 grams (0.19 g. moles) of a 19.1% active solution of an amphoteric of the formula

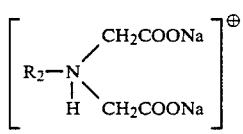

wherein $R_2$ has an alkyl chain length percent distribution as follows: $C_{10}$—2, $C_{12}$—53, $C_{14}$—24, $C_{16}$—11

$C_{18}$—10; are mixed with 40 grams (0.19 g. moles) of premelted coconut fatty acids having the alkyl chain length distribution set forth in Example I. The resulting product is a thin, opaque slurry containing 27% solids having a pH of 7.5 and is an amphoteric fatty acid complex of the formula:

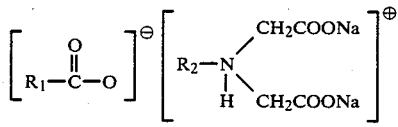

EXAMPLE VII

A clear gel hair care product is prepared as follows: 200 grams of deionized water are charged to a vessel equipped with an agitator and steam. 50 grams of a phosphate ester hydrotrope are added and the pH is adjusted to 7.0. 150 grams of Compound A are added and the solution is mixed until clear. 20 grams of polyethylene glycol 6000 distearate are added and heat is applied to the solution to 70° C. for twenty minutes. The solution is cooled to 25°–30° C. and 1.0 grams of preservative, 2.0 grams of fragrance and sufficient deionized water is added to bring the total weight to 1000 grams.

The resulting product has the following compositions:

|  | wt./wt. % |
| --- | --- |
| Compound A | 15.00 |
| phosphate ester hydrotrope | 5.00 |
| polyethylene glycol 6000 distearate | 2.00 |
| preservative | 0.10 |
| fragrance | 0.20 |
| deionized water q.s. to | 100% |

EXAMPLE VIII

An opaque liquid soap is prepared having the following formulation:

|  | wt./wt. % |
| --- | --- |
| Compound A | 15.00 |
| Compound C | 15.00 |
| Cabosil (tradename for colloidal silica, available from Cabot Corp., Boston, Mass.) | 3.50 |
| isopropanol | 0.10 |
| fragrance | 0.30 |
| deionized water q.s. to | 100% |

The pH of the above formulation is adjusted to 6.5 with citric acid.

EXAMPLE IX

A clear, liquid hair cleanser composition is prepared having the following formulation:

|  | wt./wt. % |
| --- | --- |
| Compound A | 5.00 |
| polyoxyethylene 80 sorbitan monolaurate | 10.00 |
| Deriphat 160 (tradename for salt of N—alkyl beta-iminopropionic acid available from General Mills Inc., Kankekee, Illinois) | 5.00 |
| polyethylene glycol 6000 distearate | 2.00 |
| benzyl alcohol | 0.10 |
| Dowicil 200 (tradename for the cis isomer of 1-(3-chloroalkyl)-3,5,7-triaza-1-azoniaadamantine chloride) | 0.10 |
| fragrance | 0.20 |
| deionized water q.s. to | 100% |

The above formulation is adjusted to a pH of 7.1 with 15% HCl and has a viscosity of 413 cps. at 25° C. and is a slight ocular irritant. The formulation also exhibits good foam properties.

EXAMPLE X

A detergent bar composition is prepared as follows: 50 parts of Compound A are mixed with 20 parts of Deriphat in a steam jacketed mixer at a temperature of 70° C. After the slurry is homogeneous, 10 parts of polyoxyethylene (80 sorbitan monopalmitate are added followed by the addition of 10 parts each of talc and dextrin. The batch is mixed 20 minutes, cooled, milled into ribbons and pressed into detergent bars.

The resulting bars have the following formulation:

|  | wt./wt. % |
| --- | --- |
| Compound A | 50.00 |
| Deriphat 160 | 20.00 |
| polyoxyethylene (80) sorbitan monopalmitate | 10.00 |
| talc | 10.00 |
| dextrin | 10.00 |
|  | 100.00 | and has a pH of 7.0. This product is a moderate irritant and exhibits excellent foaming properties.

EXAMPLE XI

In order to demonstrate the synergism of the amphoteric-fatty acid complexes of the present invention with respect to foam characteristics, compounds A and B, the amphoteric portion thereof and the coconut fatty acid portion thereof were individually tested in accordance with the modified Ross-Miles foam test set forth hereinbefore.

The results are shown in Table I below:

TABLE I

| Compound | % Active | Initial foam Normal Water and Grease | Height (mm) Hard Water 200 ppm $CaCO_3$ |
| --- | --- | --- | --- |
| amphoteric of compound A | 5.0 | 295 | 343 |
| coconut fatty acid | 5.0 | 0 | 0 |
| compound A | 5.0 | 353 | 358 |
| amphoteric of compound B | 5.0 | — | 295 |
| coconut fatty acid | 5.0 | — | 0 |
| compound B | 5.0 | — | 360 |

EXAMPLES XII–XX

The following compositions are prepared by admixing the surfactant components, adjusting the pH to 7.2±0.2 with dilute acid or base as required and adding deionized water to 100%:

|  | % wt/wt. EXAMPLES | | | | | | | | |
| --- | --- | --- | --- | --- | --- | --- | --- | --- | --- |
|  | XII | XIII | XIV | XV | XVI | XVII | XVIII | XIX | X |
| Compound B | 5.0 |  |  |  |  | 2.5 | 2.5 | 2.5 | 2.5 |
| lauryl succinic acid |  | 5.0 |  |  |  | 2.5 |  |  |  |
| disodium sulfococoate |  |  | 5.0 |  |  |  | 2.5 |  |  |
| lauryl ether (4) carboxylate |  |  |  | 5.0 |  |  |  | 2.5 |  |
| lauryl disodium sulfosuccinate |  |  |  |  | 5.0 |  |  |  | 2.5 |
| deionized water | q.s. to 100% | | | | | | | | |

EXAMPLE XXI

The compositions prepared in Examples XII–XX are tested for hard water foam properties using the modified Ross-Miles procedure set forth hereinbefore and the results are as follows:

| Example | Initial Foam Height in mm 200 ppm hard water |
| --- | --- |
| XII | 358 |
| XIII | 330 |
| XIV | 348 |
| XV | 330 |
| XVI | 330 |
| XVII | 365 |
| XVIII | 375 |
| XVX | 368 |
| XX | 378 |

As can be readily seen from the results above, the compositions containing a mixture of the specific amphoteric-fatty acid complexes and the anionic surfactants of the present invention (Examples XVII–XX) exhibit a synergistic increase in initial foam height. It is also observed that the quality of the foam generated by the compositions of the present invention is superior to that of the other compositions in that it is denser and creamier. A generated foam of this nature is not only perceived to be better by the consumer, but is also capable of supporting and suspending soils in a manner superior to the more open, lace-like foam of the compositions of Examples XII–XVI and thus these soils are more easily removed.

EXAMPLE XXI

A detergent bar composition is prepared by charging to a steam-jacketed rotary mixer 23.7 parts by weight stearic acid, 13.3 parts by weight dextrin, 35.1 parts by weight disodium α-sulfococoate, 14.2 parts by weight compound A, 0.2 parts titanium dioxide and 10.0 parts water. The mixture is heated to 50°–60° C. and mixed until homogeneous and the pH is adjusted to 7.2±0.2 with 50% NaOH solution. The resulting product is chilled, rolled in flakes, milled, plodded and stamped into bars having the following composition:

|  | % wt/wt |
| --- | --- |
| stearic acid | 23.7 |
| dextrin | 13.3 |
| disodium α-sulfococoate | 35.1 |
| Compound A | 14.2 |
| TiO$_2$ | 0.2 |
| 50% NaOH | 5.2 |
| deionized water | 8.3 |
|  | 100.0 |

The resulting bar foams copiously in hard and soft water and free of lime soap deposits and is also found to be a slight ocular irritant when tested.

EXAMPLE XXII

A detergent bar composition is prepared in accordance with the procedure of Example XXI and has the following formulation:

|  | % wt/wt |
| --- | --- |
| Compound B | 20.00 |
| stearic acid | 15.00 |
| polyethylene glycol 4000 | 5.00 |
| dextrin | 10.00 |
| talc | 10.00 |
| disodium lauryl sulfosuccinate | 35.00 |
| deionized water | 5.00 |
|  | 100.00 |

The pH is adjusted to about 6.5 utilizing 50% NaOH solution.

EXAMPLE XXIII

A liquid cream soap product is prepared as follows: 87.5 parts by weight of compound C and 20.0 parts by weight of lauryl succinic acid are charged to a vessel equipped with a stirrer and steam and are heated to 45° C. The pH is adjusted to 7.0±0.2 with dilute NaOH followed by the addition of 1 part of propylene glycol and 95 grams of deionized water. The mass is cooled to 30° C. and 2 parts of a fragrance are added prior to filling into tubes. The resulting product has the following formulation:

|  | % wt/wt |
| --- | --- |
| Compound C | 42.57 |
| lauryl succinate | 9.73 |
| propylene glycol | 0.48 |
| fragrance | 0.97 |
| deionized water q.s. to | 100% |

The product is a smooth opaque mild cream gel easily dispensed from tubes.

EXAMPLE XXIV

An opaque liquid soap is prepared having the following formulation:

|  | % wt/wt |
| --- | --- |
| Compound D | 30.0 |
| lauroyl sarcosinate | 20.0 |
| polyethylene glycol 6000 distearate | 3.0 |
| deionized water q.s. to | 100 |

The pH of the above formulation is adjusted to 6.5 with dilute HCl.

EXAMPLE XXV

An opaque liquid soap is prepared having the following formulation:

|  | % wt/wt |
| --- | --- |
| disodium lauryl sulfosuccinate | 3.00 |
| Compound A | 2.50 |
| ammonium lauryl (3) ether sulfate | 3.00 |
| polyoxyethylene 80 sorbitan monolaurate | 5.00 |
| preservative | .10 |
| dye and fragrance | .25 |
| deionized water q.s. to | 100 |

The pH of the above formulation is adjusted to 6.5 with dilute HCl.

EXAMPLE XXVI

A conditioning shampoo composition is prepared having the following formulation:

|  | wt/wt % |
| --- | --- |
| Compound A | 7.45 |
| Sodium lauryl sulfate | 6.60 |
| disodium lauryl sulfosuccinate | 5.80 |
| Dowicil 200 | .10 |
| hydroxypropylmethylcellulose | .50 |
| sodium chloride | .50 |
| ethylene glycol monostearate | .60 |
| polyoxyethylene (80) sorbitan monolaurate | .18 |
| dye | .01 |
| tetra sodium salt of ethylenediamine tetra acetic acid | .06 |
| fragrance | .50 |
| deionized water q.s. to | 100 |

The above formulation is adjusted to a pH about 7.8±0.1 with HCl or NaOH as needed and has a viscosity of about 4000 cps. at 25° C. and is a slight ocular irritant. The formulation exhibits excellent foaming and conditioning properties.

In addition to the preferred embodiments described herein, other embodiments, arrangements, and variations within the spirit of the invention and the scope of the appended claims will occur to those skilled in the art.

What is claimed is:

1. A complex of the formula

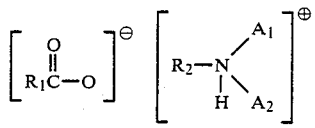

wherein $R_1$ is alkyl containing from about 5 to 17 carbon atoms and mixtures thereof; $R_2$ is alkyl amido of the formula

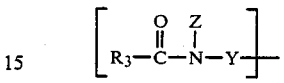

wherein $R_3$ is alkyl containing from about 5 to 17 carbon atoms and mixtures thereof; Z is H or lower alkyl containing from 1 to 4 carbon atoms; and Y is alkylene containing from 2 to 4 carbon atoms;

$A_1$ and $A_2$ are the same or different and at least one of $A_1$ and $A_2$ are selected from the group of anionic salt moieties consisting of

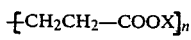

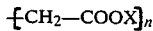

wherein X is a water soluble cation and n is an integer of 1 or 2 with the proviso that if only one of $A_1$ and $A_2$ are selected from the anionic salt moieties above, the other is lower alkyl or lower hydroxyalkyl containing from 1 to 4 carbon atoms.

2. The complex of claim 1 wherein $R_1$ is a mixture of coconut alkyl chain lengths.

3. The complex of claim 1 wherein $R_1$ is a mixture of tallow alkyl chain lengths.

4. The complex of claim 1 wherein $A_1$ and $A_2$ are $CH_2COONa$.

5. The complex of claim 1 of the formula

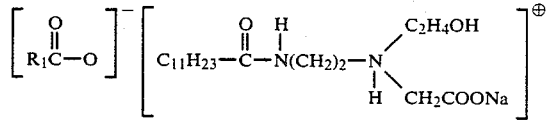

wherein $R_1$ is a mixture of alkyl chain lengths of from $C_5H_{11}$—$C_{17}H_{35}$.

* * * * *